(12) United States Patent
Yu et al.

(10) Patent No.: US 9,364,412 B2
(45) Date of Patent: Jun. 14, 2016

(54) ELECTROSTATICALLY CONTROLLED HYDROGELS

(75) Inventors: Yihua Bruce Yu, Salt Lake City, UT (US); Sivakumar Ramachandran, Salt Lake City, UT (US); Yiider Tseng, Gainesville, FL (US)

(73) Assignees: University of Utah Research Foundation UT (US); THE JOHNS HOPKINS UNIVERSITY, Baltimore, MD (US)

( * ) Notice: Subject to any disclaimer, the term of this patent is extended or adjusted under 35 U.S.C. 154(b) by 1312 days.

(21) Appl. No.: 12/085,049

(22) PCT Filed: Nov. 14, 2006

(86) PCT No.: PCT/US2006/044265
§ 371 (c)(1),
(2), (4) Date: May 14, 2008

(87) PCT Pub. No.: WO2007/059171
PCT Pub. Date: May 24, 2007

(65) Prior Publication Data
US 2009/0169625 A1    Jul. 2, 2009

Related U.S. Application Data

(60) Provisional application No. 60/736,817, filed on Nov. 14, 2005.

(51) Int. Cl.
| | |
|---|---|
| *A61K 31/7088* | (2006.01) |
| *A61K 38/00* | (2006.01) |
| *A61K 31/56* | (2006.01) |
| *A61K 9/10* | (2006.01) |
| *A61K 8/64* | (2006.01) |
| *A61K 8/04* | (2006.01) |
| *A61K 9/00* | (2006.01) |

(52) U.S. Cl.
CPC . *A61K 8/64* (2013.01); *A61K 8/042* (2013.01); *A61K 9/0009* (2013.01)

(58) Field of Classification Search
None
See application file for complete search history.

(56) References Cited

U.S. PATENT DOCUMENTS 6,333,194 B1 * 12/2001 Levy et al. .................... 435/450
7,884,185 B2 * 2/2011 Schneider et al. ............ 530/326

FOREIGN PATENT DOCUMENTS

WO    WO2006/116524    * 11/2006

OTHER PUBLICATIONS

Sanborn et al. "In situ crosslinking of a biomimetic peptide-PEG hydrogel via thermally triggered activation of factor XIII", Biomaterials, 23, 2002, 2703-2710.*
Ramachandran et al., "Repeated Rapid Shear-responsiveness of Peptide Hydrogels with Tunable Shear Modulus", Biomacromolecules, 6, 2005, pp. 1316-1321.*
Caplan et al. "Control of self-assembling oligopeptide matrix formation through systematic variation of amino acid sequence", Biomaterials, 23, 2002, pp. 219-227.*
Ryadnov et al. ""Belt and Braces": A Peptide-Based Linker System of de Novo Design", JACS, 125, 2003, pp. 9388-9394.*
Wand et al., High-resolution of NMR of encapsulated proteins dissolved in low-viscosity fluids, PNAS, 1998(95), 15299-15302, (1998).

* cited by examiner

*Primary Examiner* — Bethany Barham
*Assistant Examiner* — Melissa Javier
(74) *Attorney, Agent, or Firm* — Ballard Spahr LLP

(57) ABSTRACT

The compositions and methods disclosed herein pertain to the manufacture and use of hydrogels. The disclosed compositions and methods pertain to hydrogels capable of induction by a variety of methodologies, such as by pH, salt and/or mixing. Such hydrogels are capable of self- or co-assembly and while doing so, may entrap a variety of bioactive agents in their native form, such as proteins, DNA, RNA and the like. The hydrogels of the present invention also demonstrate rapid sheer-responsiveness. The hydrogels of the present invention are biodegradable, biocompatible and useful as a biomaterial or drug-delivery device.

8 Claims, 21 Drawing Sheets

Figure 18A-D
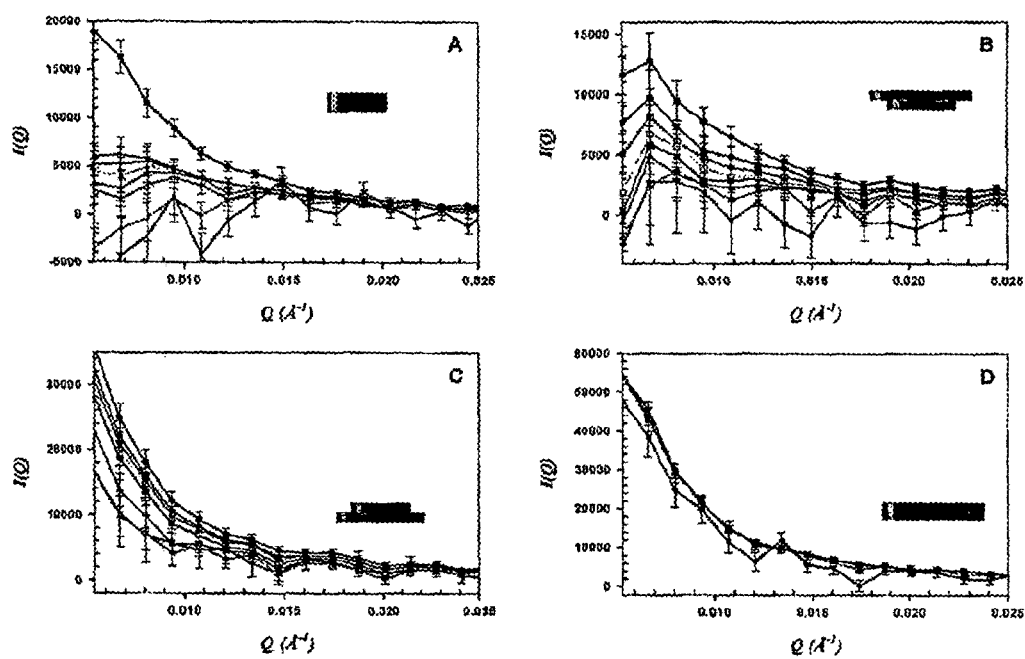

ELECTROSTATICALLY CONTROLLED HYDROGELS

CROSS-REFERENCE TO RELATED APPLICATIONS

The present application is a U.S. national phase filing under 35 U.S.C. 371 of International Patent Application No. PCT/US2006/044265, filed Nov. 14, 2006, which claims the benefit of U.S. Provisional Patent Application No. 60/736,817, filed Nov. 14, 2005, each of which are hereby incorporated by reference in their entirety.

STATEMENT REGARDING FEDERALLY SPONSORED RESEARCH

This invention was made with government support under grant number EB004416, awarded by the National Institutes of Health. The Government has certain rights to this invention.

BACKGROUND OF THE INVENTION

Field of the Invention

The present invention relates to compositions and methods for the manufacture of hydrogels, and, specifically to the ability of such hydrogels to demonstrate rapid shear-responsiveness, and to further be capable of entrapping and preserving bioactive agents, such as proteins, in their native form.

BACKGROUND

Hydrogels containing bioactive agents have gained interest in the medical field as a delivery device due to their inherent ability to biodegrade and be reabsorbed. Naturally-occurring biomaterials based on protein or peptide self-assembly are numerous in nature, such as the formation of collagen in the extra-cellular matrix and fibrin associated with the clotting of blood.

Hydrogels may also function as molecular scaffolds for directing cellular orientation and organization during tissue growth and repair. In an in-vivo setting, it may be necessary for such hydrogel structures to form and remain in place under physiologically relevant conditions of chemistry, temperature or other perturbations, such as shear- or load-induced stress.

Control of the self-assembly process, whether in the man-made or natural context, is key to a successful end-product and failure to control this process results in numerous disease states, such as Alzheimer's disease. However, it has been difficult to create self-assembling hydrogels capable of incorporating bioactive agents in their native form as formation of the hydrogel often causes conversion of the bioactive agent to an inactive form due to a change in the environmental conditions once the hydrogel has formed. Hydrogels capable of maintaining physiologically relevant conditions, such as pH, temperature, ionic strength, and the like, during the self-assembly process are greatly needed for in-vivo applications.

SUMMARY OF THE INVENTION

In the present invention, a modular design was utilized to create self- or co-assembling hydrogels. Such hydrogels are capable of preserving physiologically relevant conditions, such as the pH, ionic strength, temperature, and the like in order to support the native environment of a bioactive agent. In one embodiment, such hydrogels demonstrate rapid shear-responsiveness. In another embodiment, the hydrogels are capable of stimuli-triggered material assembly. In a particular embodiment, the components of said hydrogels assemble into a hydrogel in response to a trigger such as a change in pH, ionic concentration and/or physical contact with another module. In another embodiment, the hydrogels of the present invention further include a bioactive agent. In a further embodiment, such hydrogel itself includes bioactive agents. Such bioactive agents may be preserved in their native conformation. In another embodiment, the hydrogels are biocompatible, biodegradeable and/or may be used as a biomaterial.

DETAILED DESCRIPTION

In accordance with the purpose(s) of this invention, as embodied and broadly described herein, this invention, in one aspect, relates to compositions and methods for the manufacture and use of hydrogels capable of self-assembly and wherein said hydrogel maintains an environment conducive to a bioactive agent and demonstrates rapid shear responsiveness. Such hydrogels may also be triggered to form and/or disassemble by cues such as a change in the pH and/or ionic concentration, as well as by mixing modules that make up said hydrogel. The hydrogels themselves may also be composed of bioactive agents.

Particular advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

FIGURES

The following drawings form part of the present specification and are included to further demonstrate certain embodiments. These embodiments may be better understood by reference to one or more of these drawings in combination with the detailed description of specific embodiments presented herein.

FIG. 1 illustrates a far UV circular dichroism spectra of 1 wt % peptide solutions in 30 mM ammonium acetate aqueous buffer, pH 6.0, 25° C. according to an embodiment of the present invention.

FIG. 2 illustrates various means of inducing hydrogelation according to several embodiments of the present invention. The exemplary vials were all placed upside down for all illustrated experiments. The gel samples for all examples were in a solution of 30 mM ammonium acetate aqueous buffer, pH 6.0, with a total peptide concentration of 1 wt % with the exception of the gel made by adding NaCl to SEQ ID NO 1, which had a peptide concentration of 1.25 wt %. For salt-induced gelation, the final NaCl concentration for the SEQ ID NO 2 sample was 1.5M and that for the SEQ ID NO 1 sample was 3M (previous experimentation had shown that at 1.5M salt concentration, SEQ ID NO 1 was still a viscous solution). The illustration appears to indicate that the pH-induced gelation is reversible, forming an on/off switch mechanism for gelation.

FIG. 3 illustrates the viscoelastic properties of co-assembled hydrogels formed by mixing 0.5 wt % of each peptide in 50 mM cacodylate buffer pH 6 according to an embodiment of the present invention (total peptide concentration in the hydrogel was 0.5 wt % with the concentration of each peptide module being 0.25 wt %.

Figure 6:
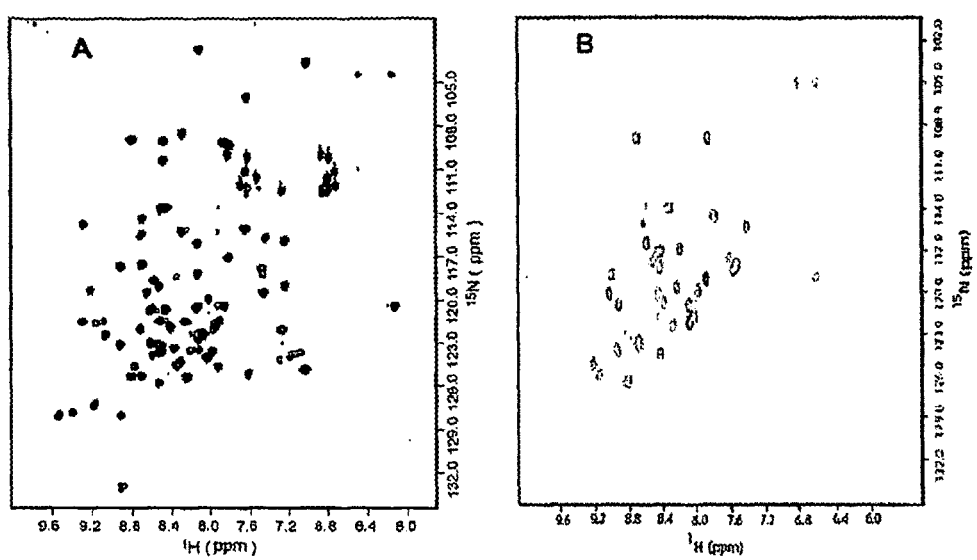

FIG. 6 illustrates the $^1H$-$^{15}N$ HSQC spectra of backbone amide of $^{15}N$-enriched ubiquitin at 25° C. according to exemplary embodiments of the present invention. (A) Overlay of ubiquitin in solution (black) and ubiquitin entrapped in a mixing-induced hydrogel (red). (B) Ubiquitin entrapped in a pH-induced hydrogel. It appears the mixing-induced hydrogel better preserves the native conformation of entrapped ubiquitin than the pH-induced hydrogel.

Figure 7:
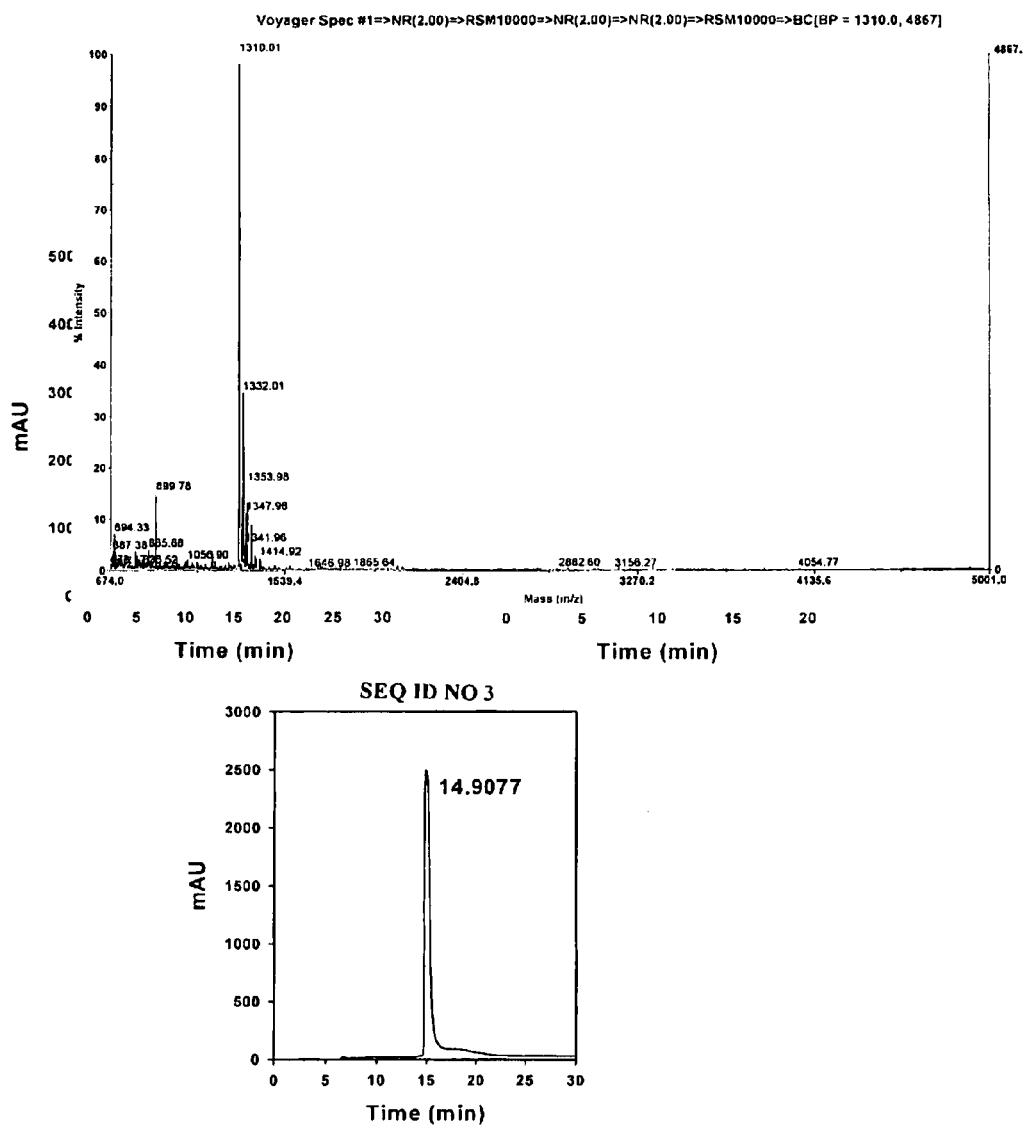

FIG. 7 illustrates analytical reversed-phase HPLC chromatogram of oligopeptides utilized in various experiments that were acquired with HP1100 chromatograph system (Agilent Technologies). Column: Zorbax 300SB-C18 (4.6×250 mm i.d.) according to various embodiments of the present invention. Elution profiles were monitored at 210 nm. Eluents for SEQ ID NO 3 and SEQ ID NO 2: solvent A: 0.05% trifluoroacetic acid (TFA) in water, pH 2.0; solvent B: 0.05% TFA in acetonitrile, pH 2.0. Eluents for SEQ ID NO 1: solvent A: 30 mM $NH_4HCO_3$ in water, pH 7.0; solvent B: 30 mM $NH_4HCO_3$ in water (40%)+acetonitrile (60%) mixture, pH 7.0. Chromatograph run conditions for all the peptides illustrated a flow rate of 1 ml/min; gradient: 2% B/min; temperature: ambient.

Figure 8:
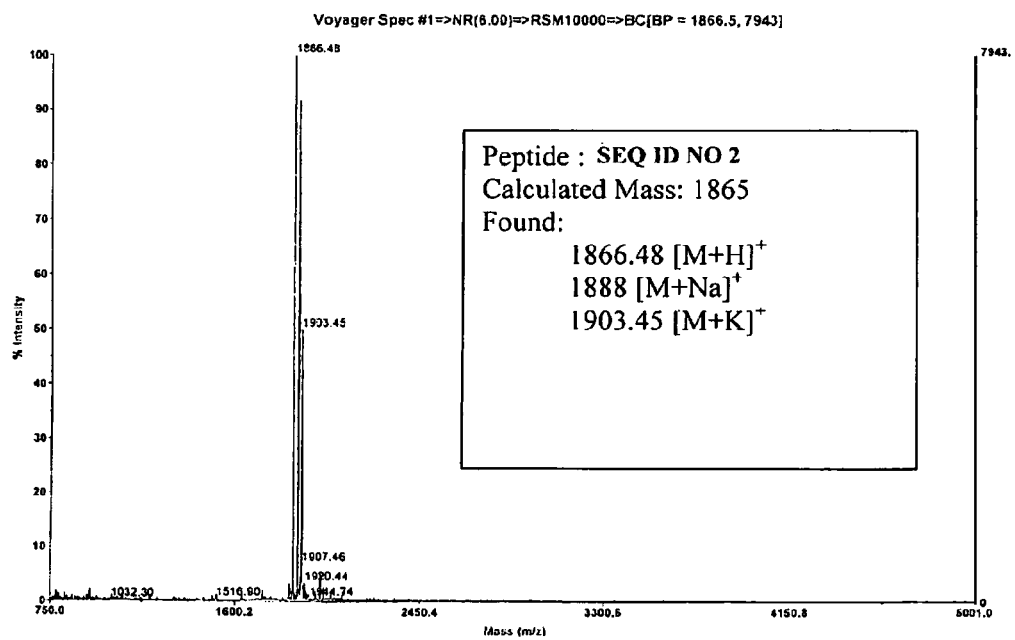
Figure 8:
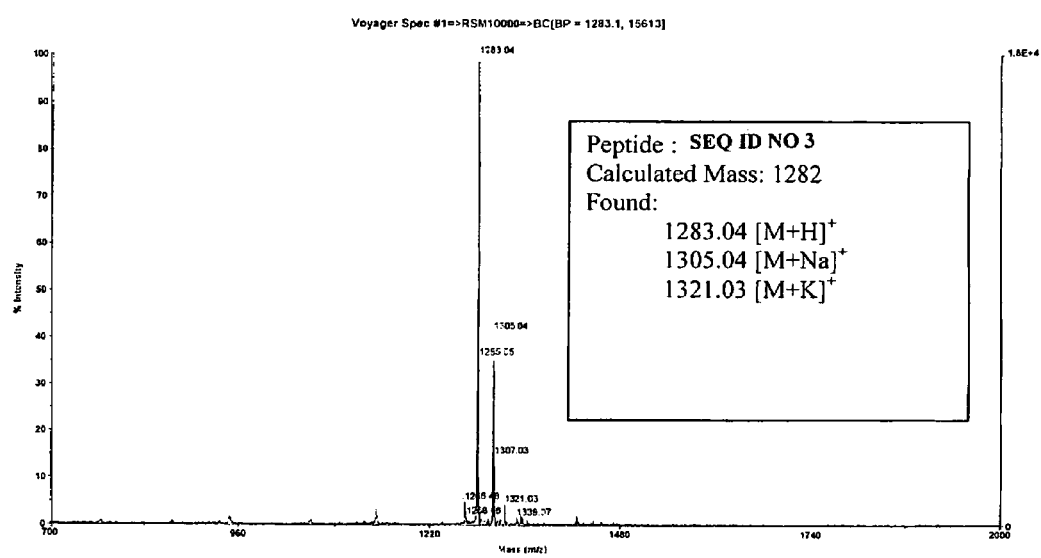

FIG. 8 illustrates matrix-assisted laser desorption ionization mass spectrometry (MALDI-MS) performed with Perseptive Biosystems Voyager-DE™ STR MALDI Mass Spectrometer according to an embodiment of the present invention. MALDI experiments were performed by mixing each peptide solution with α-cyano-4-hydroxy cinnamic acid and irradiating each sample with nitrogen laser at 337 nm. Detection was in the positive ion mode, with an accelerating voltage of 20 kV. Since the oligopeptides have multiple chargeable groups, adduct ions of sodium and potassium were apparent.

Figure 9:
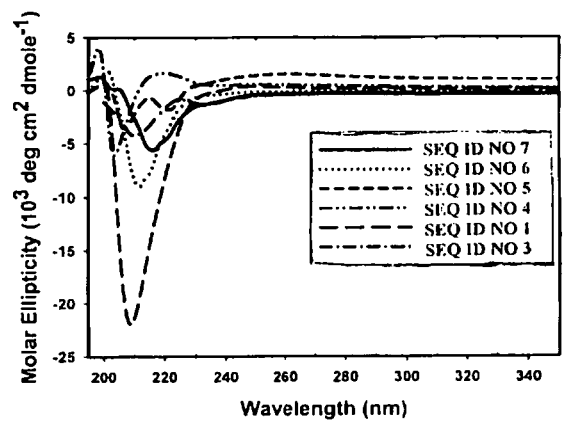

FIG. 9 illustrates the far UV circular dichroism spectra of 1 wt % peptide solutions (SEQ ID NO 4, SEQ ID NO 5, SEQ ID NO 6, SEQ ID NO 7) in 50 mM phosphate buffer, pH 6, 25° C. and 1 wt % SEQ ID NO 3 and SEQ ID NO 1 peptide solutions in 30 mM ammonium acetate buffer pH 6, 25° C. according to an embodiment of the present invention. The solubility of the SEQ ID NO 3 peptide did not appear to be high enough at pH 7. Conversely, when valine was replaced by alanine, serine or proline, solubility at pH 7 did not appear to be an issue. Due this observation, physical characterizations of the peptides in further experiments were conducted around pH 6.

Figure 10:
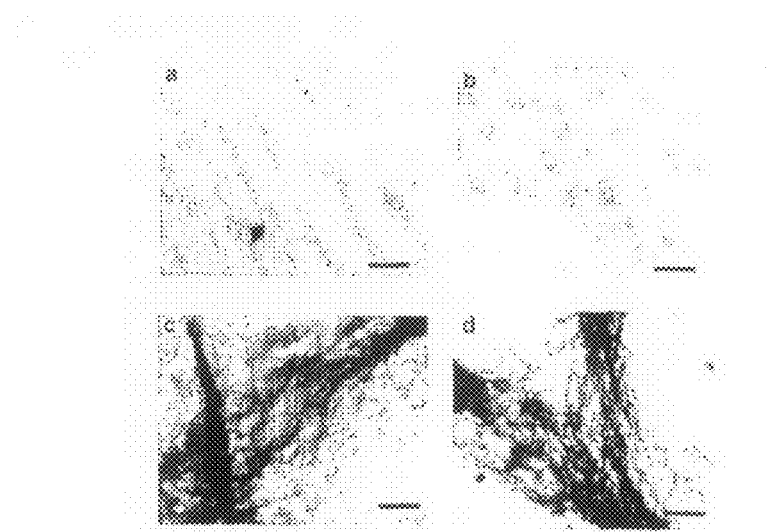

FIG. 10 illustrates Transmission Electron microscopic images of peptide samples (solution and gel) prepared in pH 6 buffer according to an embodiment of the present invention. (a) 1 wt % SEQ ID NO 3 solution, (b) 1 wt % SEQ ID NO 1 solution, (c) 0.25 wt % SEQ ID NO 3: SEQ ID NO 1 gel, (d) 0.5 wt % SEQ ID NO 3:SEQ ID NO 1 gel according to an embodiment of the present invention. The scale bar in each figure represents 1 μm.

Figure 11:
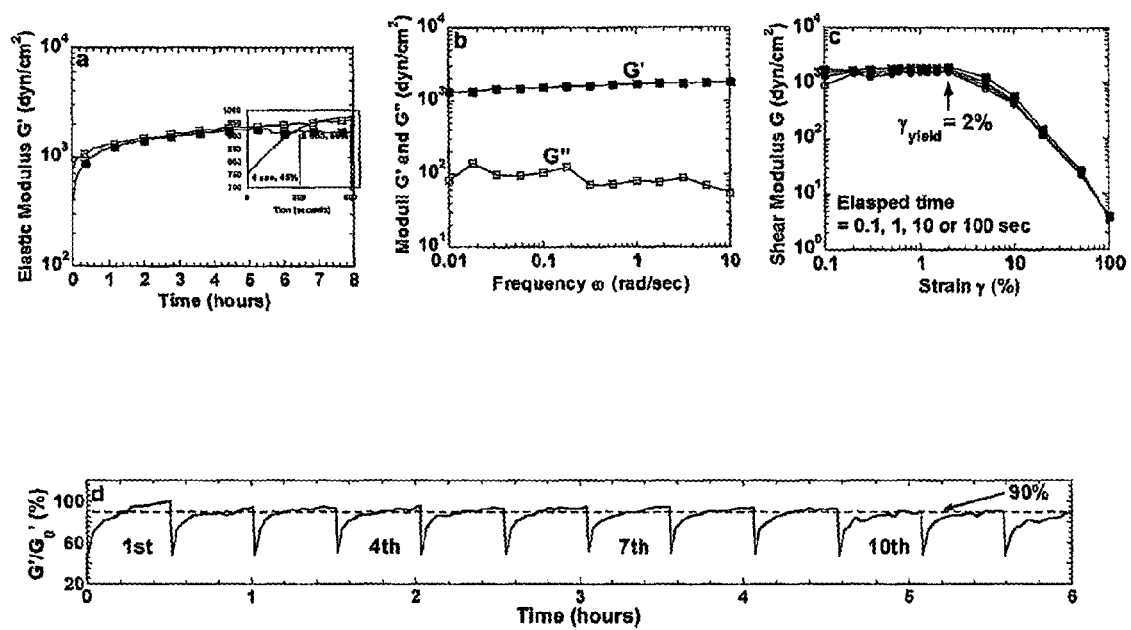

FIG. 11 illustrates the viscoelastic properties of a hydrogel assembled from SEQ ID NO 3:SEQ ID NO 1 decapeptide pair according to an embodiment of the present invention. (a) Comparison of the original gelation curve (■) with the first recovery curve (o) after the hydrogel was subjected to 100% shear (pH 6). (b) Elastic (G') and viscous (G") moduli versus frequency (ω) at an applied strain γ of 0.2% (pH 6). (c) Shear Modulus G versus strain γ according to an embodiment of the present invention. The arrow points to the yielding strain at which the hydrogel appeared to start to breakdown (pH 6). (d) 12 cycles of hydrogel recovery from shear-induced breakdowns (pH 5.5). The dashed line denotes 90% of the original elasticity value ($G_0'$) after 30 minutes of gelation. The total peptide concentration was 0.25 wt % for all the measurements. Recoverability appeared to be obtained at both pH 6.0 and 5.5 with no significant difference. This pH insensitivity would appear to indicate that such mixing-induced hydrogels are applicable over a wider range of solution conditions.

Figure 12:
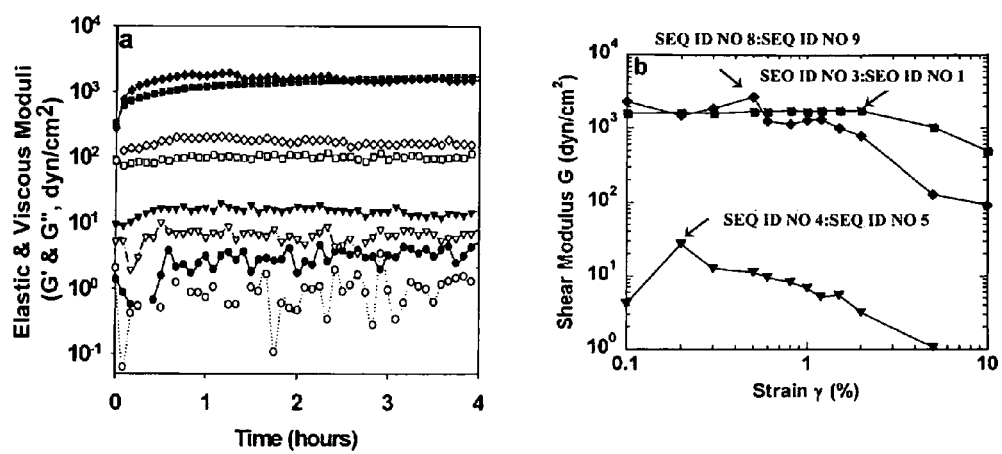

FIG. 12 illustrates (a) time sweep measurement of different peptide pairs prepared in 50 mM phosphate buffer according to an embodiment of the present invention. Filled symbols represent G' and open symbols represent G". ■/□ represent the SEQ ID NO 3:SEQ ID NO 1 pair (pH 6.0), ◆/◇ represent the SEQ ID NO 8:SEQ ID NO 9 pair (pH 7.0), ▼/▽ represent the SEQ ID NO 4:SEQ ID NO 5 pair (pH 7.0) and ●/○ represent the SEQ ID NO 6:SEQ ID NO 7 pair (pH 6.0). The total peptide concentration was 0.25 wt % for all the measurements. FIG. 12 also illustrates (b) Strain sweep measurement of different peptide pairs in 50 mM phosphate buffer SEQ ID NO 3:SEQ ID NO 1 (0.25 wt %, pH 6.0, ■, $\gamma_{yield}$→2%), SEQ ID NO 8:SEQ ID NO 9 (0.25 wt %, pH 7.0, ◆, $\gamma_{yield}$→0.4%), SEQ ID NO 4:SEQ ID NO 5 (1 wt %, pH 7.0, ▼, $\gamma_{yield}$→0.2%), arrows point to the yield value ($\gamma_{yield}$) of the peptide pairs according to an embodiment of the present invention.

Figure 5:
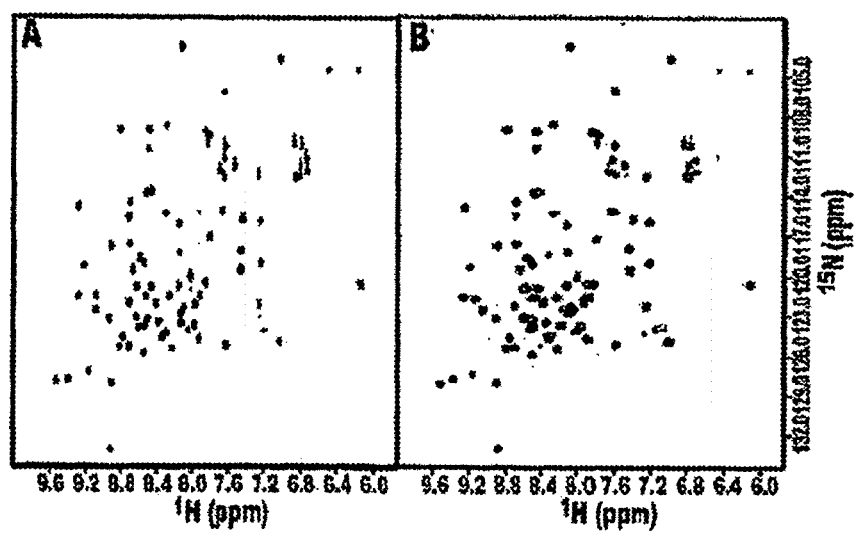
FIG. 5 illustrates the $^1H$-$^{15}N$ HSQC spectra of ubiquitin at 25° C. in solution (A) and in mixing-induced hydrogel (B) according to exemplary embodiments of the present invention.
Figure 13:
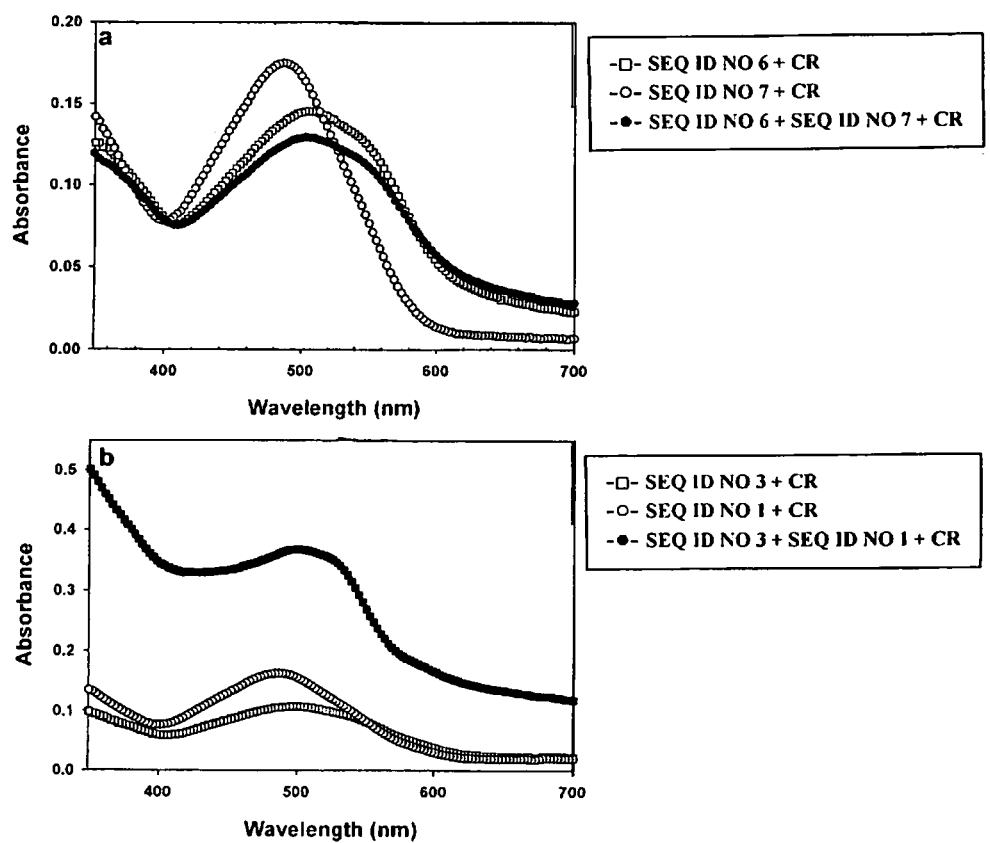

FIG. 13 illustrates a Congo Red (CR) dye binding experiment (a) SEQ ID NO 6:SEQ ID NO 7 decapeptide pair with CR in 50 mM phosphate buffer pH 6.0 according to an embodiment of the present invention. FIG. 5 also illustrates (b) SEQ ID NO 3:SEQ ID NO 1 decapeptide pair with CR in 50 mM ammonium acetate buffer pH 6.0 according to an embodiment of the present invention. The total peptide concentration was 0.25 wt % (~1947 μM) and CR concentration was 0.0071 wt % (25 μM) for all the measurements. Hyperchromic shift of the CR absorption spectrum appears to be present in the SEQ ID NO 3:SEQ ID NO 1 pair.

Figure 14:
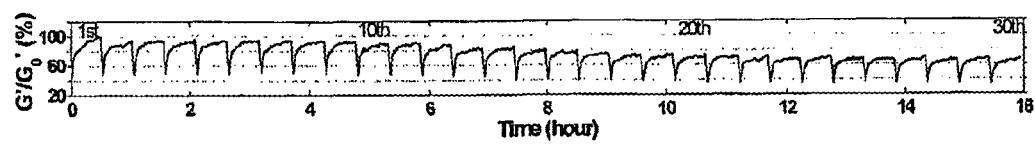

FIG. 14 illustrates repeated recovery of the hydrogel from shear-induced breakdowns according to an embodiment of the present invention. Thirty cycles of hydrogel recovery are shown here. $G_0'$ denotes the value of the initial elastic modulus after 30 minutes of gelation. The gradual decrease of G' is likely caused by water evaporation from the hydrogel sample inside the rheometer. The sample volume in the rheometer decreased from 1.4 ml to 1.2 ml during the course of measurement, which lasted ca. 16 hours. HPLC analysis of recuperated hydrogel samples after rheological measurements showed no sign of peptide degradation. As shown by FIG. 3a, the initial gelation curve and the first recovery curve appear to almost overlap. Similarly, if we overlay any two consecutive recovery curves in FIG. 3d and FIG. 14, they are almost identical. Hence, it appears that the hydrogel formed by the SEQ ID NO 3:SEQ ID NO 1 pair can recover rapidly from shear-induced breakdowns and is not affected by the slow water evaporation from the rheometer.

Figure 15:
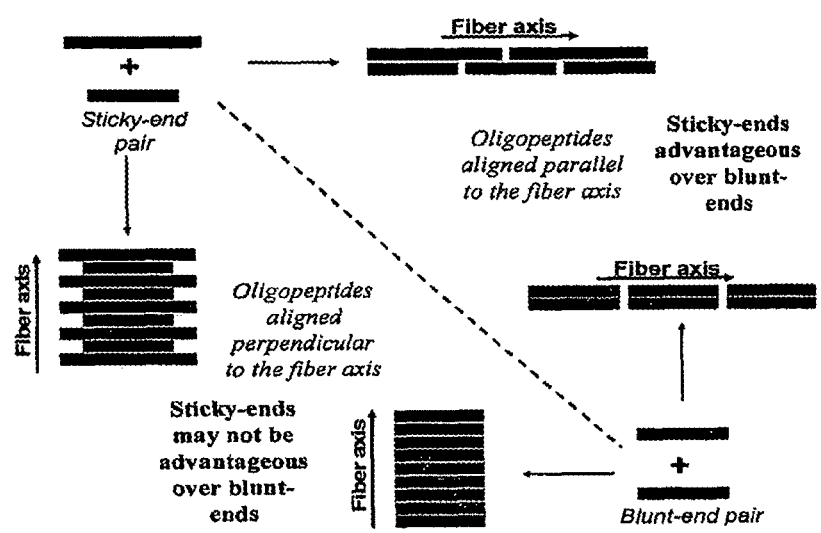

FIG. 15 illustrates possible alignment of sticky- and blunt-ended oligopeptides in the nano-fibers—perpendicular or parallel orientation of peptide chains with respect to the fiber axis according to an embodiment of the present invention. Sheet conformations are not considered as it is not supported by electron microscope and SAXS data.

FIG. 16 illustrates dynamic time sweep measurement of a) the initial gelation measured at 0.2% strain amplitude and 1 rad/sec angular frequency and b) elastic modulus of $23^{rd}$ gelation (midpoint of cycles 13 to 32 of repeated shear-induced breakdown recovery cycles) according to an embodiment of the present invention. The total peptide concentration was 0.25% wt/wt. Positive and negative modules were mixed at equal molar ratio.

Figure 17:
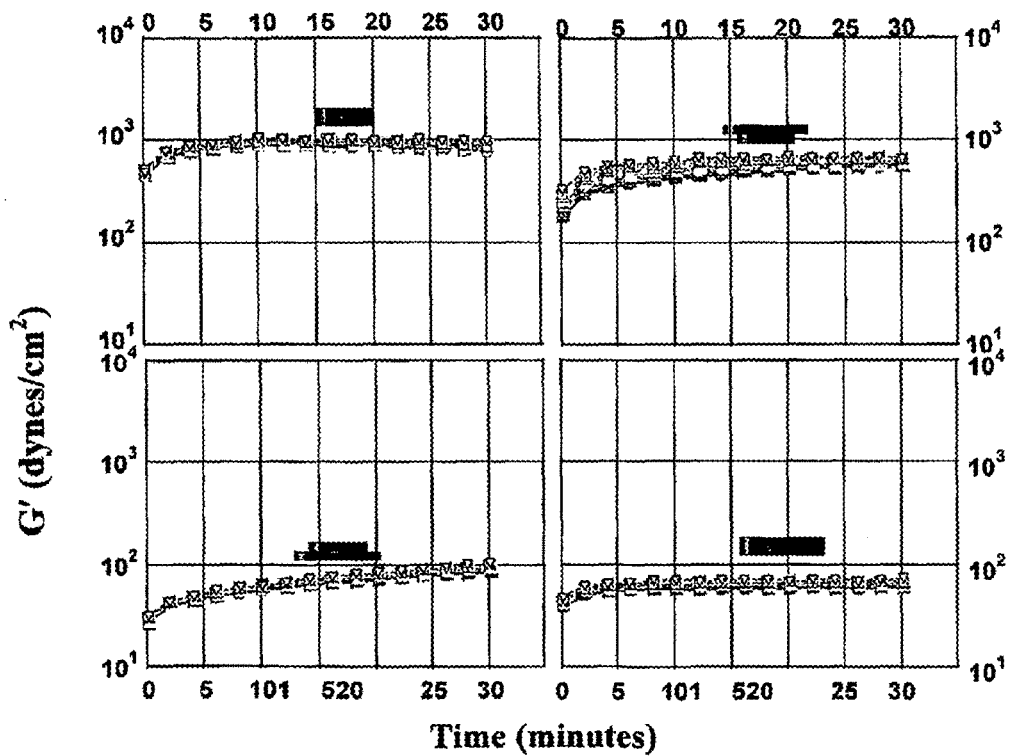

FIG. 17 illustrates overlay of recovery profiles from repeated shear-induced breakdowns (200% strain) according to an embodiment of the present invention. Shown here are recovery profiles of the 13th to 32nd breakdown-recovery cycles.

FIG. 18 illustrates time evolution of I(Q) vs Q during the process of co-assembly according to an embodiment of the present invention. 15 min—brown, inverted triangle; 1 hr—light blue, crossed triangle; 3 hr—pink, triangle; 5 hr—dark blue, crossed square; 7 hr—yellow, square; 9 hr—green, crossed circle; 11 hr—red, circle; 24 hr—black circle.

Figure 19A:
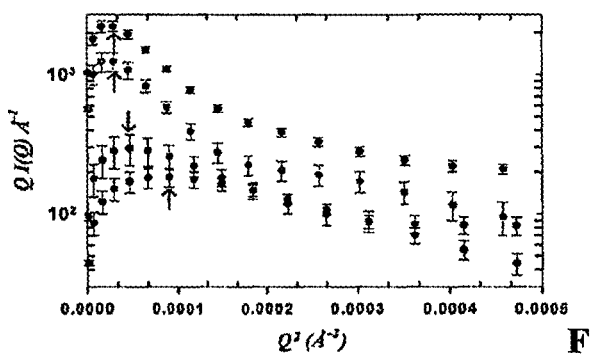

FIG. 19 illustrates small Angle X-ray Scattering (SAXS) data from each of the four biomaterial at 0.25% wt/wt total peptide concentration—(A) Guinier plot of the slit-desmeared scattering data for each of the four biomaterials at 24 hrs (data were desmeared). Arrows indicate the roll-over points; (B) Log I(Q)-Log Q plot to show the mass-fractal, power-law dependent decay of I(Q) for each co-assembled hydrogel (24 h after mixing) according to various embodiments of the present invention.

Figure 20:
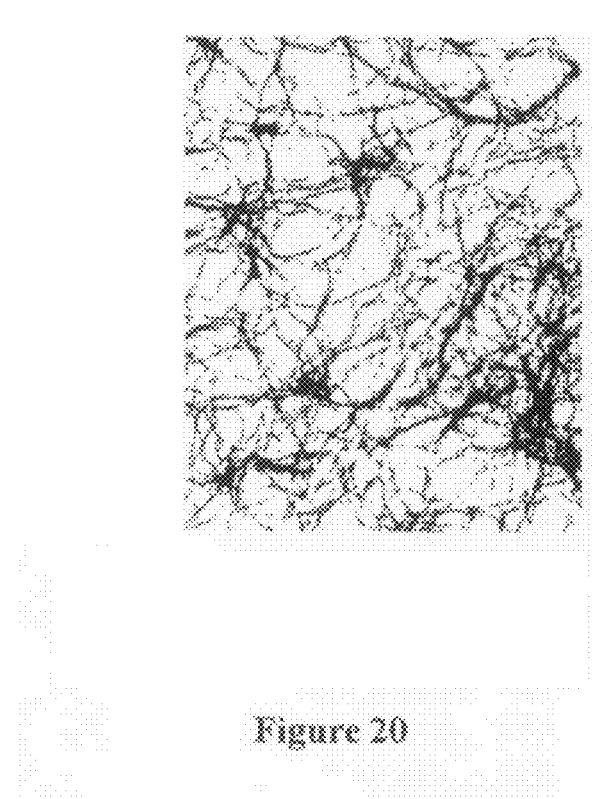

FIG. 20 illustrates a representative Transmission Electron Microscopic image of SEQ ID NO 10:SEQ ID NO 11 gel showing a heterogeneous fibrous network according to an embodiment of the present invention.

DEFINITIONS

For the purposes of the present invention, the following terms shall have the following meanings:

For the purposes of the present invention, ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

For the purpose of the present invention, the term, "bioactive agent" refers to one or more agents associated with a hydrogel of the present invention. Examples include proteins, DNA, RNA, steroids, and the like.

For the purpose of the present invention, the terms, "hydrogelation," "gelation," "self-assembly," and "co-assembly" refers to any physical phenomenon that results in the formation of a hydrogel.

Moreover, for the purposes of the present invention, the term "a", "an" or "the" refers to one or more of that entity; for example, "a protein" or "an inhibitor" refers to one or more of those elements or at least one element. As such, the terms "a" or "an", "one or more" and "at least one" can be used interchangeably herein. It is also to be noted that the terms "comprising," "including," and "having" can be used interchange-
ably. Furthermore, an element "selected from the group consisting of" refers to one or more of the elements in the list that follows, including mixtures (i.e. combinations) of two or more of the elements.

Reference will now be made in detail to particular embodiments of the invention.

The present invention embodies compositions and methods related to novel hydrogels. In one embodiment, the hydrogels of the present invention are produced utilizing a modular design. In a particular embodiment, the modular design includes mixing-induced material assembly whereby two modules are mixed together in order to produce a hydrogel of the present invention. In a particular embodiment, each module includes electrostatic charges, such as in the bioactive agent.

Applicant herein incorporates by reference the SEQ ID material on the compact disk named Sequence Listing that includes the file 007180-54 US SEQ IDS_ST25 (1-2-09).txt (3.95 KB) created on Jan. 12, 2009.

Table 1 below includes exemplary peptides with electrostatic charges.

TABLE 1

Sequences of oligopeptides.

| Sequence | |
|---|---|
| *Sequences of Positively Charged Modules* | |
| SEQ ID NO 2 | Acetyl-KWKVKVKVKVKVKVK-amide |
| SEQ ID NO 3 | Acetyl-WKVKVKVKVK-amide |
| SEQ ID NO 11 | Acetyl-KWKAKAKAKAKAKAK-amide |
| SEQ ID NO 8 | Acetyl-WKAKAKAKAK-amide |
| *Sequence of a Negatively Charged Module* | |
| SEQ ID NO 1 | Acetyl-EWEVEVEVEV-amide |
| SEQ ID NO 10 | Acetyl-WEAEAEAEAEAEAEA-amide |
| SEQ ID NO 9 | Acetyl-EWEAEAEAEA-amide |

In one embodiment, bioactive agents carry multiple negative charges, multiple positive charges or both negative and positive charges. The numbers in Table 1 represent the chain length of the exemplary peptides that compose the particular hydrogels. Modular assembly of hydrogels containing such peptides may be achieved by pairing a positive module with a negative module. Positively charged amino acids are indicated by a "+" sign. Table 1 illustrates the versatility of modular assembly as peptides with equal chain length and unequal chain length were co-assembled to create blunt- and sticky-end pairs, respectively. K—Lysine, V—Valine, E—Glutamic acid, W—tryptophan. Table 2 illustrates some possible pairings of peptide modules:

TABLE 2

Possible pairing of oligopeptides
Possible pairing of sequence

Blunt-ended pairs

SEQ ID NO 10:SEQ ID NO 11
SEQ ID NO 9:SEQ ID NO 8

Sticky-ended pairs

SEQ ID NO 9:SEQ ID NO 11
SEQ ID NO 10:SEQ ID NO 8

In this embodiment, assembly of peptide modules of equal chain length results in peptide modules which may have enhanced mechanical properties, including kinetic and structural features. The optimal chain length of the modules for such assembly is about 10 amino acid residues.

The modules of the present invention may be based on the mutual attraction and self-repulsion of the two modules. For instance, there may be an alternating charge/apolar sequence pattern as illustrated by the pair of decapeptide modules illustrated below in Table 3:

TABLE 3

Exemplary Sequence Patterns

| Positively-charged peptide module | Negatively-charged peptide module |
|---|---|
| Acetyl-WK(VK)$_4$-amide<br>SEQ ID NO 3 | Acetyl-EW(EV)$_4$-amide<br>SEQ ID NO 1 |

In this particular embodiment, the separation of positively charged (K) and negatively charged (E) side chains into two independent modules results in the peptide modules being mutually attractive but also self-repulsive. This will function to promote the self-assembly process upon mixing the two modules together. High net charge density in the side chains of each peptide may also enhance the long-range attraction of the two oppositely charged modules. Construction of a hydrogel in this manner may also increase the solubility of such hydrogel. Exact sequence matching is also not necessary for the production of this particular hydrogel due to the repetitiveness of each individual module. The self-repulsion will also prevent spontaneous self-assembly as each individual module has no attraction for itself. Gelation will only occur upon mixing the two modules together.

The electrostatic charges carried by a particular module, including a bioactive agent included with one or more individual modules, may act as a brake mechanism to inhibit spontaneous hydrogelation or aggregation of the component modules.

In another embodiment, the electrostatic control mechanism may be overcome with a triggering event. In a particular embodiment, such triggering event comprises one or more of a change in pH (pH-induced gelation), a change in ionic strength (salt-induced gelation), physical contact with another module (mixing-induced gelation), and the like.

pH-induced hydrogelation may be triggered by exposure to an acid or base. It may also be triggered by any other redox or electron donor/withdrawing reaction in general. Such acid or base may be in the form of a liquid, solid, vapor and the like. The hydrogel once triggered to form by exposure to an acid or base that alters the pH, may later be triggered to deconstruct by exposure to acids or bases once again. In a particular embodiment utilizing peptides as a bioactive agent, d-amino acids may be inserted in the peptide sequence to increase the degradation rate of such hydrogel.

Salt-induced hydrogelation may be triggered by exposure to any salt solution. In one embodiment, such salt solution is sodium chloride. In a particular embodiment, various polar residues of the hydrogel components may be selectively optimized so that gelation occurs under salt concentrations that would be present during in-vivo conditions. The sodium chloride solution may be added to the peptide solution such that the final peptide concentration in the hydrogel is 1 wt %.

Mixing-induced hydrogelation includes the mixing of any two or more modules together in any ratio. In a particular embodiment, such modules are mixed together at a 1:1 weight ratio such that the final bioactive agent concentration is 1 wt %.

The hydrogels of the present invention are biocompatible.
The hydrogels of the present invention are biodegradable.
The hydrogels of the present invention may further include a bioactive agent. In a particular embodiment, such bioactive agent comprises one or more of proteins, steroids, DNA, RNA, ribonucleosides, drugs, pharmaceuticals, and other physiologically relevant molecules. In another particular embodiment, such bioactive agent is not affected by hydrogelation. For example, if a protein or peptide is utilized, the native conformation of such protein or peptide will be maintained as illustrated by 2D NMR fingerprinting methodology. As such, bioactive agents delivered by hydrogels of the present invention may retain bioactivity once in situ. When constructing a hydrogel to further include a bioactive agent to one or more of the modules, the polarity of such bioactive agent must be kept in mind as it may affect gelation.

The hydrogels of the present invention may be used as a biomaterial. They may also be utilized as a drug-delivery device. They may also be utilized as encapsulation matrices for applications where preservation of the conformation of a bioactive agent is critical. Such matrices include drug delivery of a bioactive agent, tissue engineering, structural genomics (as alignment media for NMR characterization) and the like.

In an embodiment of the present invention, the modular design of the hydrogels, including their electrostatic control, allow for the construction of dynamic libraries of peptide-based hydrogels. These hydrogels may provide both biodegradability and bio-resorbability, as well as the ability to fine tune the material properties, such as the sol-gel transition pH, ionic strength, kinetics of co-assembly, and the like, via systematic sequence variation in the bioactive. In a particular embodiment, such bioactive agent is a peptide. In another particular embodiment, such systemic sequence variation is of the constitutive peptide modules themselves. In pH- and salt-induced hydrogels, the material property may be fine tuned by changing the peptide sequence, length and concentration. In mixing-induced hydrogels, material properties may be further tuned by varying concentration- and length-ratios of the pairing peptide modules, offering additional flexibility in adjusting the material property.

In another embodiment of the present invention, the fibrillar structure and high elasticity of these hydrogels mimic the extracellular matrix and can act as a morphogenetic guide during tissue regeneration.

The hydrogels of the present invention may further include additional agents helpful to tissue regeneration. In a particular embodiment, such agent is a cell adhesive motif, like arginine, glycine, aspartic acid (RGD) which can be incorporated into the sequences for specific tissue engineering applications. If the bioactive agent is a peptide or protein, the entrapment in its near native state in the hydrogel (FIG. 5A) and the rapid gelation time (FIG. 3) may be highly desirable for tissue engineering and drug delivery applications.

In one embodiment, the hydrogels are capable of responding to mechanical stress. In particular embodiments, the hydrogels will recover quickly after application of stress, rather than breaking under shear stress. The novel ability of the hydrogels of the present invention to regain mechanical strength after repeated shear-induced breakdowns will provide a biomaterial for many uses. This further allows for the use of the hydrogels of the present invention as scaffolds for tissue engineering as they can accommodate cell growth without breaking upon application of stress.

In another embodiment, the modules that form the hydrogels are capable of self-assembly and then the hydrogel is capable of disassembling. The ability to assemble and then disassemble is useful for applications where shear-stress is great, such as in tissue engineering scaffolds. Such disassembly may make the scaffold more elastic for cell motility and/or cell-to-cell interactions.

EXAMPLES

The following examples are included to demonstrate particular embodiments of the invention. It should be appreciated by those of skill in the art that the techniques disclosed in the examples which follow represent techniques discovered by the inventors to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the invention.

Preparation of Oligopeptides

All the peptides were synthesized using standard Fmoc Chemistry on Rink Amide MBHA resin and purified using High Performance Liquid Chromatography (HPLC). The purity and molecular weight of each purified peptide was verified by analytical HPLC and mass spectrometry, respectively. Each purified peptide sample was then dissolved in its respective buffer at appropriate pH and dialyzed at room temperature for 2-4 hours using a dialysis membrane with a molecular weight cutoff of 100 Da. The concentration of each peptide sample was later determined based on the UV absorption of the Trp residue in each peptide, using an extinction coefficient of 5690 $M^{-1} \cdot cm^{-1}$ at 280 nm, with light scattering corrected.

Preparation of $^{15}$N-Enriched Ubiquitin

The gene encoding human ubiquitin, a 76 amino acid protein, was subcloned into the commercial plasmid pET11a in the polyclonal region between NdeI and BamHI. See Wand, et al., PNAS 1998(95): 52299-15302 (1998). In addition to the main coding sequence, a nucleotide segment that specifies six consecutive histidine residues (6×His) was engineered at the C-terminal of the amino acid sequence that supports highly efficient purification using nickel nitriloacetic (Ni-NTA) affinity chromatography. The resulting plasmid was then used to transform E. coli BL21(DE3). Overexpression on a minimal media (M9) prepared using $^{15}$NH$_4$Cl provided a means for generating uniformly $^{15}$N-enriched ubiquitin protein product. Approximately 20 mgs of purified ubiquitin was obtained per liter of culture (approximately 4×600 µl, 1 mM samples).

Modes of Gelation—pH-, Salt-, and Mixing-Induced

For pH-induced gelation, dialyzed peptide solutions in vials were exposed to vapors of acetic acid (acid-induced gelation) or ammonium hydroxide (base-induced gelation). To demonstrate the reversibility of pH-induced gelation, acid- and base-induced hydrogels were exposed to vapors of ammonium hydroxide and acetic acid, respectively. For salt-induced gelation, saturated sodium chloride solution was added into the dialyzed stock peptide solution so that the final peptide concentration in the hydrogel was 1 wt %. For mixing-induced gelation, dialyzed peptide solutions were mixed at 1:1 weight ratio such that the final total peptide concentration was 1 wt %.

Circular Dichroism Spectroscopy

Circular dichroism (CD) spectra were obtained using an AVIV 62DS spectropolarimeter equipped with a water bath operated at 25° C. A cylindrical cell of 0.1 mm path length was used for the measurements. The instrument was calibrated using ammonium d-10-camphor sulfonate (0.06% w/v) before use and flushed with nitrogen during operation. Ellipticity measurement was normalized to mean residue ellipticity (θ), expressed in unit of $deg \cdot cm^2 \cdot dmole^{-1}$.

Rheological Characterization

Rheological studies of hydrogels were conducted by loading freshly mixed peptide-pairs into a 50 mm cone-and-plate module of a strain-controlled, software-operated rheometer (ARES-100; TA instrument, Piscataway, N.J.), followed immediately by an 8-hour of time sweep test, with an applied strain of 0.2% amplitude at a 1 rad/sec frequency.

For determination of viscoelastic properties, the hydrogel samples were sequentially subjected to an 8-hour of time sweep test, a frequency sweep test (frequency from 0.01 to 10 rad/sec) and a series of stress relaxation tests with a defined step-strain (with amplitudes at 0.1, 0.2, 0.3, 0.5, 0.6, 0.8, 1, 1.2, 1.5, 2, 5, 10, 20, 50 and 100%, respectively). In time sweep tests, the applied strain had a 0.2%-amplitude at a 1-rad/sec frequency. Frequency sweep tests were conducted at 0.2%-amplitude and the data was acquired at a log mode with 4 data points per frequency decade. A shear modulus G versus strain profile was analyzed according to previously published procedures. G was acquired from the stress relaxation tests at elapsed time of 0.1, 1, 10, and 100 seconds, respectively. Afterwards, another 8-hour of time sweep test at 0.2% strain and 1 rad/sec frequency was conducted as a recovery test.

To characterize the responsiveness of the hydrogel from repeated shear-induced breakdowns, the peptide mixture was allowed to gel for 4 hours (under 0.2%-amplitude strain and 1 rad/sec frequency) and consequently subjected to a routine of recovery cycles for more than 15 hours (FIG. 20). Each cycle consisted of a 2-minute break period with a continuous 200% sine-wave strain, and a 30-minute recovery period with a constant 0.2% strain at 1 rad/sec frequency. The magnitude of the shear force (200%-amplitude) and the duration of the break and recovery periods (2 and 30 minutes, respectively) were based on results from strain sweep and recovery tests.

Congo Red Dye Binding Experiment

Concentration of Congo Red dye (CR) stock solution in 50 mM phosphate or ammonium acetate buffer at pH 6 was obtained using an extinction co-efficient value of 59300 $M^{-1} \cdot cm^{-1}$ at 505 nm. Peptide samples dialyzed in appropriate buffers were mixed with CR stock solution such that in each experiment the total concentration of peptide was 0.25 wt % (~1947 µM) and that of CR was 0.0071 wt % (25 µM).

Transmission Electron Microscopy

Transmission electron microscopy (TEM) images were acquired from a Hitachi H7100 electron microscope operated at 75 KV accelerating voltage. Each sample (a thin layer of gel or solution) was placed on a 200 mesh copper grid and negatively stained with uranyl acetate for one hour. The samples were left to dry in a desiccator before acquiring TEM images.

Small Angle X-Ray Scattering (SAXS)

A small-angle x-ray scattering instrument was used for measurements at 25° C. This instrument has a slit geometry and all analyses were corrected for this. The angular dependence of the scattering of x-rays from particles in a solvent has the form:

$$I(Q) = \left| \left\langle \int_V (\rho(\vec{r}) - \rho_s) e^{-i\vec{Q}\cdot\vec{r}} d^3r \right\rangle \right|^2 \quad (1)$$

where $\rho(\vec{r})$ is the scattering length density of the scattering particle as a function of atomic position ($\vec{r}$) and $\rho_s$ is the mean scattering length density of the solvent. Q is the momentum transfer vector, having the magnitude $4\pi(\sin\theta)/\lambda$, where $2\theta$ is the scattering angle and $\lambda$ is the wavelength of the incident X-ray (CuK$\alpha$=1.54 Å). The integration over the particle volume, V, is rotationally averaged for un-oriented particles and the experiment measures the time and ensemble average for all particles in the sample. The inverse Fourier transform of I(Q) gives the pair distance or vector length distribution function, P(r), for the scattering particle:

$$P(r) = \frac{1}{2\pi^2} \int I(Q) Q \cdot r \sin(Q \cdot r) dQ \quad (2)$$

P(r) can be calculated using indirect Fourier transform methods. The r value at which P(r)=0 gives the maximum linear dimension for the scattering particle, $d_{max}$. The zeroth and second moments of P(r) are the zero angle scattering intensity (I(0)) and the radius of gyration of the scattering particle ($R_g$), respectively. I(0) is proportional to the molecular weight of the scattering particles.

The scattering data also were subjected to both Guinier and mass fractal analysis. Guinier showed that one can approximate the scattering from rod-shaped particles (i.e. one dimension of the particle is much larger than the other two) in the small-Q region as:

$$Q \cdot I(Q) = I_c(0) \cdot e^{-\frac{Q^2 R_c^2}{2}} \quad (3)$$

where $R_c$ is the radius of gyration of cross-section of the rod. $I_c(0)$ is proportional to mass per unit length.

Mass-fractal analysis can be used to analyze materials that have a repetitive mass unit such as might be anticipated in these hydrogels. The scattering data were fitted to mass fractal power-law decay using the following equation:

$$I(Q) = B_f Q^{-d_f} \quad (4)$$

where, $d_f$ is the fractal dimension of the object and $B_f$ is the power-law scaling prefactor characteristic of the fractal dimensionality of the scattering structure. $d_f$=1 signifies a stiff rod-like structure and $B_f$ in this case is proportional to the length and fourth power of the diameter of the rod; $d_f$=2 signifies either a disk- or Guassian-coil shaped object; $d_f$=1.5 signifies a swollen Guassian-coil in good solvent. In the case of Guassian-coils ($d_f$=2 or 1.5), $B_f$ is proportional to the end-to-end distance of the Guassian-coil.

Example 1

Determination of the Structure of Peptides Before and After Gelation Induced by Several Physiological Triggers To characterize ubiquitin entrapped in mixing-induced hydrogels, solutions of two peptide modules (SEQ ID NO 3 & SEQ ID NO 1) and a solution of ubiquitin were mixed thoroughly and then loaded into an NMR tube to allow gelation. The total peptide concentration and the ubiquitin concentration were both 0.25 wt % in the gelled sample.

To characterize ubiquitin entrapped in pH-induced hydrogels, a solution of one peptide module (SEQ ID NO 2) and a solution of ubiquitin were mixed into an NMR tube. The NMR tube was then exposed to ammonium hydroxide vapor to induce gelation. The peptide concentration and ubiquitin concentration were both 1 wt % in the gelled sample.

All samples contained 7.5% of $D_2O$ to support $^2H$ lock. A Varian INOVA 500 MHz NMR spectrometer equipped with triple-axis pulsed-field gradient (TRIAX) indirect probe was used to acquire $^1H$-$^{15}N$ HSQC spectra. The spectral width in the $^1H$ dimension was 7000 Hz (~14 ppm) with the carrier frequency set at the water resonance. Water suppression was accomplished using a flip-back type scheme. Spectral width in the $^{15}N$ dimension was 2000 Hz (~39.5 ppm) with the carrier frequency set at 121 ppm, which corresponds approximately to the center of peptide/protein amide frequency range. The $^1H$-$^{15}N$ HSQC spectrum of ubiquitin in 50 mM, pH 6 phosphate buffer was also acquired.

Figure 1:
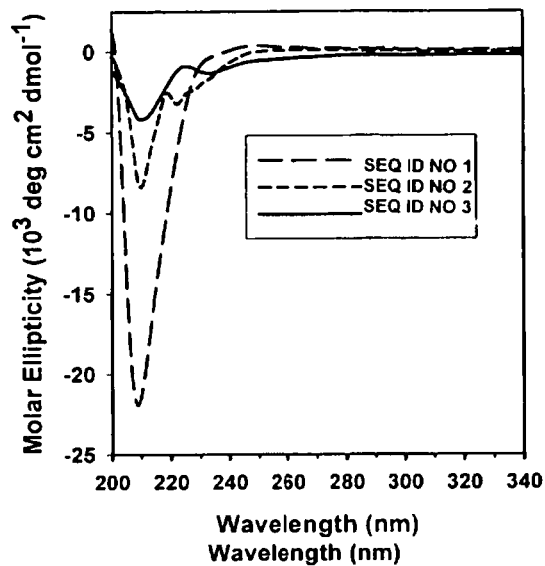

It appeared all peptides had a random coil conformation while still in solution as analyzed by an AVIV 62DS spectropolarimeter equipped with a water bath operating at 25 C. A circular dichroism spectra was observed as shown in FIG. 1.

Various means were utilized to induce hydrogelation. Multiple gelation modes were produced by removal of electrostatic inhibition in three ways, alteration of pH, addition of salt and combination of two gelation modes as shown in FIG. 2.

Figure 2:
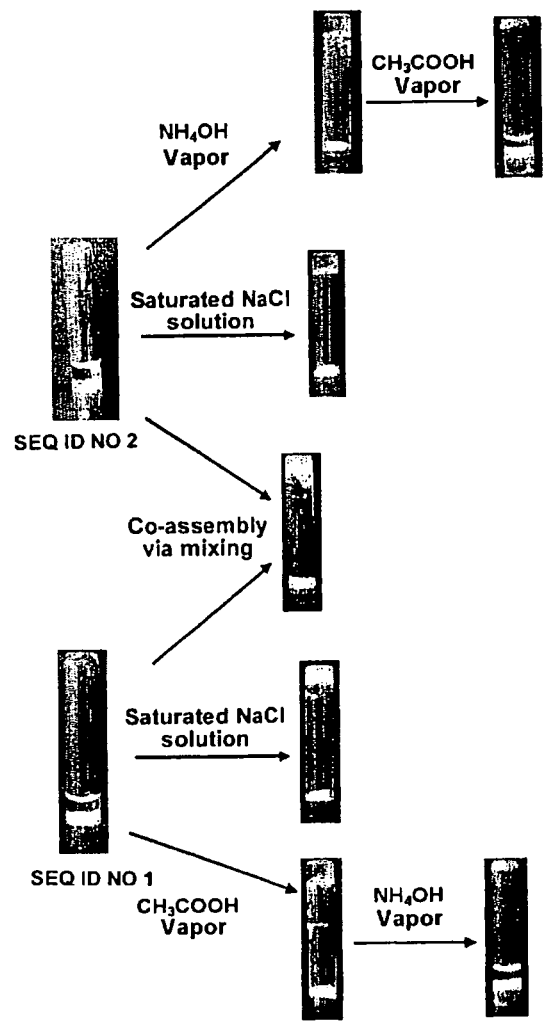

The salt concentration necessary to induce gelation was quite high as indicated by FIG. 2. All peptides were dialyzed in 30 mM buffer and needed a much higher concentration to trigger hydrogelation. The final NaCl concentration for the SEQ ID NO 2 sample was 1.5 M and for the SEQ ID NO 1 it was 3 M. As indicated in FIG. 2, the SEQ ID NO 1 peptide samle was still a viscous solution at 1.5 M. This is in direct contrast with other self-attractive peptides currently on the market composed of the same amino acid composition and sequence pattern that are induced to form a hydrogel at salt concentrations of approximately 5 mM.

The elevated salt concentration required to trigger the hydrogels of the present invention also appears to increase the flexibility of them, in terms of bioactive agent purification, handling and preservation. For instance, the SEQ ID NO 1 peptide was purified using 30 mM $NH_4HCO_3$ buffer. This would not work for prior art hydrogels as their components would have gelled in the presence of 5 mM salt.

Example 2

Rheometric Measurement of Hydrogels of the Present Invention

The rheological gelation profiles of hydrogels of the present invention were obtained by rheometric measurement.

Figure 3:
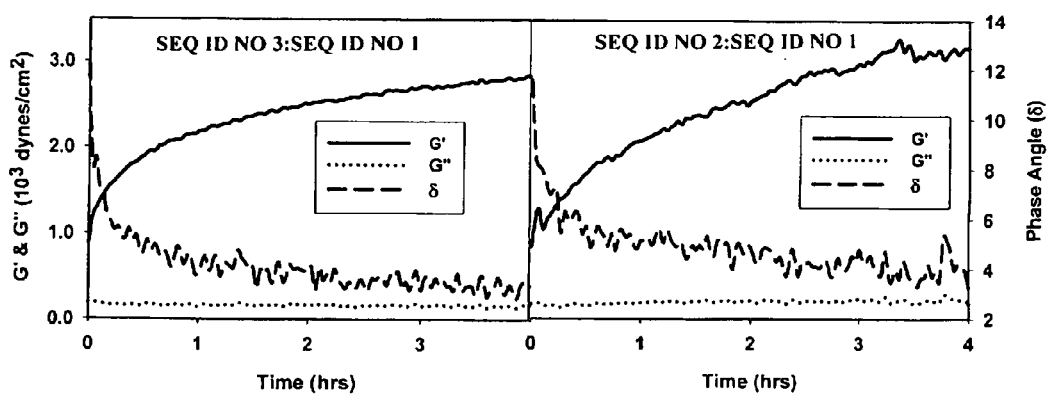

FIG. 3 illustrates the profiles of a SEQ ID NO 3:SEQ ID NO 1 pair and a SEQ ID NO 2:SEQ ID NO 1 pair. The gelation process appears smoother for the SEQ ID NO 3:SEQ ID NO 1 pair than for the SEQ ID NO 2:SEQ ID NO 1 pair. In both pairs, gelation was characterized by two regions: a rapid growth region followed by a slow growth region. The phase angle ($\delta=\tan^{-1}(G''/G')$) can be an indicator of the relative elastic and viscous components of a hydrogel. Both pairs appeared to have a very low phase angle (~5°), indicating that both hydrogels may be highly elastic. This experiment appeared to indicate that peptide pairs with blunt-ends, such as (SEQ ID NO 3:SEQ ID NO 1), and those with sticky-ends (SEQ ID NO 2:SEQ ID NO 1), are both capable of forming hydrogels upon mixing, which indicates the versatility of the compositions and methods of the present invention.

Example 3

Analysis of the Conformation of Bioactive Agents after Hydrogelation

Figure 4:
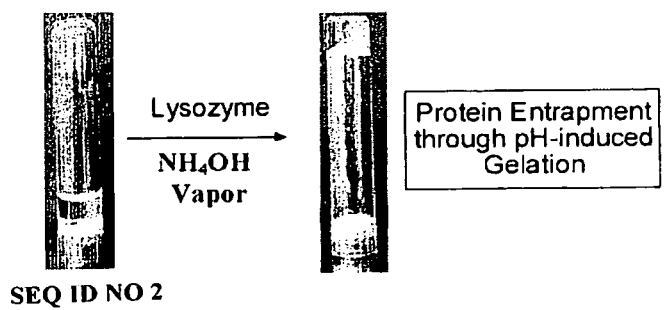
FIG. 4 illustrates the encapsulation of lysozyme by pH-induced gelation. In this exemplary embodiment, 1 wt % SEQ ID NO 2 peptide in 30 mM ammonium acetate buffer (pH 6) containing 0.5 wt % lysozyme was exposed to the vapors of ammonium hydroxide to induce gelation.

The hydrogel matrices of the present invention are capable of entrapping bioactive agents. This was analyzed utilizing two small proteins, lysozyme and ubiquitin, added to the modules during hydrogel formation (FIG. 4). To verify the retention of the native conformation of entrapped protein molecules, a $^1$H-$^{15}$N hetero-nuclear-single quantum spectrum ($^1$H-$^{15}$N HSQC) of uniformly $^{15}$N-enriched ubiquitin was used as a model system to study the integrity of the entrapped proteins in the hydrogel. Ubiquitin entrapped in the mixing-induced gel appeared to retain its native conformation, as indicated by minimal perturbation of the amide NMR resonances when compared to its native solution conformation (FIG. 5). The preservation of ubiquitin native structure is indicated from the overlay of these fingerprints in FIG. 6A. Ubiquitin entrapped in the pH-induced gel appeared to retain a native-like overall fold (FIG. 6B). However, the higher gel pH appeared to accelerate the rate of amide proton exchange, leading to the loss of a number of amide NMR resonances. The resonances of ubiquitin in hydrogel matrices appeared to be comparatively broader indicating a substantial decrease in the rotational motion of the entrapped protein. Compared to pH- or salt-induced gels, mixing-induced gels appeared to cause minimal perturbation to the medium and thereby to the entrapped bioactive agent. Although 2D NMR fingerprinting has been utilized to study the conformation of protein solutions (either alone or entrapped in reverse micelles), it also appears to be a good method of characterizing the conformation of bioactive agents entrapped inside a peptide hydrogel.

Example 4

Conformation of Peptides in Solution

FIG. 9 indicates the CD spectra of individual peptide solutions have a minimum near 205 nm and lack characteristics of any standard secondary structures, which further indicates the individual peptides are in the random coil conformation. However, the polyproline II type conformation can not be ruled out for SEQ ID NO 4 due to the presence of a weak positive band at 220 nm.

Mixing of oppositely charged peptide solutions appeared to induce the formation of a viscoelastic material. Transmission electron microscopy (TEM) was used to analyze the morphology of the co-assembled hydrogel. TEM images of the hydrogels (both 0.25 wt % and 0.5 wt %) appeared to indicate a network of nanofibrillar structures extending over several micrometers. The peptide solutions themselves did not appear to have any fibrillar structures as indicated in FIG. 10.

Example 5

Shear-Responsiveness and Resilience of Hydrogels of the Present Invention

A series of rheological measurements were conducted to evaluate the viscoelastic properties of the hydrogel formed by the decapeptide pair as indicated by FIG. 11. First, a time sweep experiment conducted at 1 rad/sec frequency and a strain of 0.2%-amplitude indicated that the elastic modulus, G', rose to ca. 750 dyne/cm$^2$ within a few seconds and reached a plateau value of ca. 1700 dyne/cm$^2$ after 3 hours as indicated in FIG. 11a.

Kinetically, the elastic modulus profile was made of an elastic burst phase on the order of seconds followed by a slower elastic growth phase on the order of a few hours as indicated on FIG. 11a. Based on previous mechanistic studies on the gelation process of proteins, the results may indicate a biphasic kinetic profile whereby the initial burst phase of elasticity may involve a rapid association of the peptide modules (due to long range electrostatic interactions) to form an uneven entangled nanofibrillar network, followed by a slow reorganization phase during which the fibrils may distribute more evenly in the network. Over time, the degree of homogeneity may increase in the hydrogel network and the elasticity may reach a plateau.

A frequency sweep conducted at a strain of 0.2%-amplitude revealed that G' appeared relatively independent of frequency ($\omega$) within the frequency range of 0.01-10 rad/sec (FIG. 11b), indicating the hydrogel had limited mobility up to 600 s ($t=2\pi/\omega$). While the plateau value of the elastic modulus G' is in the 1000 dynes/cm$^2$ range, the plateau value of the viscous modulus G'' is in the 100 dynes/cm$^2$ range (FIG. 11b), revealing an elastic, solid-like material at 0.25 wt % total peptide concentration.

To test the resilience of the hydrogel, well-spanned strains were applied 10 minutes apart in a step-incremental manner to observe how the hydrogel relaxes strains. Shear modulus plotted against strain amplitude indicated the hydrogel cannot resist a strain of over 2% and beyond this yield strain it appeared to exhibit a shear-thinning property (FIG. 11c). At 100% strain, G' dropped to 4 dyne/cm$^2$, suggesting complete disruption of the hydrogel network.

To test the recoverability of the hydrogel from shear-induced breakdowns, the completely disrupted hydrogel (by a series of step-incremental strains up to 100% amplitude) was allowed to recover for 8 hours. The elasticity profile of the recovery test was almost identical to that of the initial gelation process, indicating that the shear-induced breakdown is reversible (FIG. 11c). Further, just like the initial gelation process, the recovery process had a burst phase in which the gel obtained ca. 50% of its mechanical strength within a few seconds and a slower growth phase in which the gel obtained the rest of its mechanical strength within a few hours. To monitor repeated recoveries of G', the hydrogel underwent 30-cycles of break-and-recovery with a 2-minute strain break period followed by a 30-minute recovery period.

Based on the initial gelation and first recovery data (FIG. 11a), a 2-minute break period was chosen to ensure complete disruption of the hydrogel network and a 30-minute recovery period was chosen in order to reach the beginning of the plateau region (so that the kinetics of the recovery process can be observed). FIG. 11d indicates that G' recovered back to 90% of its original value after 12 break-recovery cycles. Even after 30 cycles, G' recovered to more than 70% of its original value (FIG. 14). In all recovery processes, the elastic burst phase was completed on the order of seconds, indicating a fast recovery of the nanofibrillar network.

Example Six

Effect of Neutral Amino Acids on Hydrogel Properties

In order to further comprehend design principles involved in this novel class of self-assembling hydrogels, the neutral amino acid residue in the sequence was varied systematically. Substitution of valine in the sequence with the less hydrophobic alanine or serine appeared to result in a weaker gel with lower G' values (FIG. 12a) and resilience (FIG. 12b). Even though the G' values for the valine and alanine pairs did not appear significantly different, the valine pair had higher yield value (2% at 0.25 wt % peptide concentration) than the alanine pair (0.4% at 0.25 wt % peptide concentration) and the serine pair (0.2% at 1 wt % peptide concentration).

On the other hand, substitution of valine with proline, another important component of natural elastomer-elastin[25] and a dominant component in collagen, did not appear to form a hydrogel (FIG. 12a). To investigate the basis of this behavior, a Congo Red dye (CR) binding experiment was performed with the valine and proline decapeptide pairs. CR is a histological stain for β-sheet type amyloid aggregates. Binding of CR to the fibrillar aggregates also causes a hyperchromic red shift in the absorption spectrum of CR. Based on the absorption spectra, individual peptide did not bind to CR (FIG. 5), in agreement with their random coil conformation as seen in CD spectra. The proline decapeptide pair did not appear to cause hyperchromic shift in the absorption spectrum of CR (FIG. 13a) whereas the valine pair appeared to cause a significant hyperchromic shift (FIG. 13b). The increased light scattering at higher wavelengths (600-700 nm) in the valine pair appears due to the increased size of the aggregates corresponding to hydrogel formation. The results indicate that even though proline has similar hydrophobicity like valine (proline has same number of saturated carbon atoms in its side chain as valine), the SEQ ID NO 6:SEQ ID NO 7 pair nonetheless did not appear capable of forming a hydrogel due to the low β-sheet propensity of proline. Hence, β-sheet propensity may be an important factor to take into consideration when designing this class of hydrogels.

Example 7

Effect of Pairing Equal and Unequal Chain Length Oligopeptides

To explore the mechanism of material assembly and determine the effect of equal and unequal chain length pairings on material properties of the bulk material, a quartet of oligopeptides was synthesized. The peptide quartet contained two positively charged modules of 10 and 15 amino acid residues long and two negatively charged modules of 10 and 15 amino acid residues long. Each positive module can pair with one negative module and hence there are four potential pairings, two of equal chain length (blunt-ended pairs) and two of unequal chain length (sticky-ended pairs). Viscoelastic properties and structural features of the hydrogels assembled from these oligo-peptide pairs were evaluated by dynamic rheometry and small-angle X-ray scattering (SAXS) techniques, respectively.

Figure 16A:
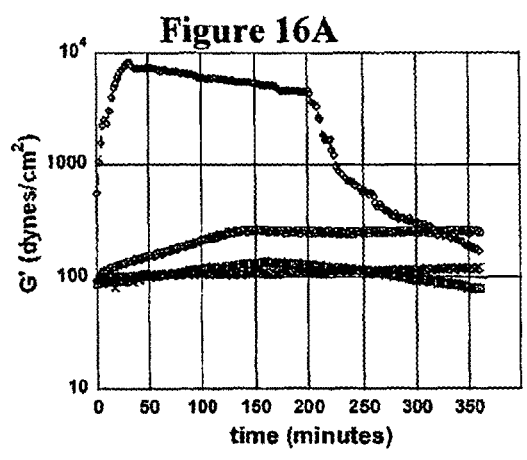
Figure 16B:
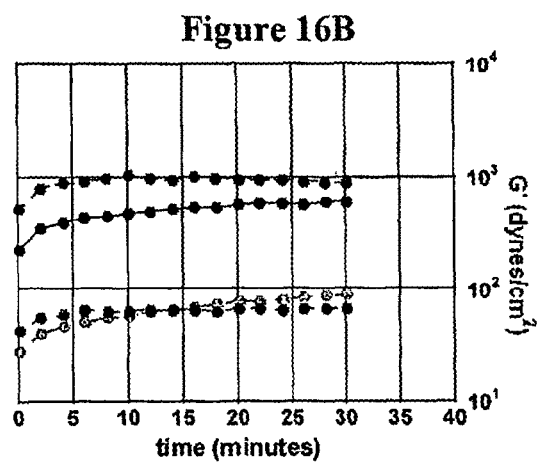

Upon mixing, each peptide pair starts to gel, as monitored by dynamic rheometry. The end points in terms of G' of the initial gelation are not very different among the four pairs (FIG. 16A). However, the gelation processes are quite different with that of the SEQ ID NO 9:SEQ ID NO 8 pair being the smoothest and that of the SEQ ID NO 10:SEQ ID NO 11 pair being the most rugged. Repeated shear responsiveness of each of these biomaterials was tested as described earlier. Each of the biomaterials regained their mechanical strength after shear-induced breakdowns. It appears that repeated shear-induced breakdowns acted as a correcting mechanism to repair initial mis-assembly. Indeed, after 13 cycles of shear-induced breakdowns and recoveries, all four hydrogels have reproducible mechanical properties in the subsequent cycles (FIG. 17). Although the initial gelation processes resulted in G' values not far apart from each other (~2-3 fold) (FIG. 16A), cycles of shear-induced breakdown-recovery resulted in stabilized G' values that are significantly different among the four pairs (~10 fold) with the following order: G'(SEQ ID NO 9:SEQ ID NO 8)>G'(SEQ ID NO 10:SEQ ID NO 8)>G'(SEQ ID NO 9:SEQ ID NO 11)>G'(SEQ ID NO 10:SEQ ID NO 11) (FIG. 16B). It appears from the rheological measurements that the SEQ ID NO 9:SEQ ID NO 8 pair forms the strongest gel and the SEQ ID NO 10:SEQ ID NO 11 pair forms the weakest gel, as judged by the stabilized G' value.

Transmission electron microscopic (TEM) images of all hydrogels show the formation of fibrous network (FIG. 20). However, the drying step involved in the sample preparation for TEM might cause peptide fibers to aggregate further, giving rise to very heterogeneous samples that were difficult to characterize accurately in terms of fiber thickness, estimated very approximately as ~30 nm (diameter). Therefore, small angle X-ray scattering (SAXS) was used to probe the hydrated fibrous network with minimal perturbations to the samples. The measured scattering intensity (I(Q)) increased over time for each of the biomaterials, indicative of the formation of aggregates and consistent with a growing fibril networks (FIG. 18). Each of the peptide pairs shows evidence for the development of structures having long-range order that gives rise to small-angle scattering profiles that reached equilibrium over approximately a 24-hour period. The trend of the gelation kinetics is evident in FIG. 18, and also in the summary of the structural parameters that can be determined using P(r) analysis (Table 4). The kinetics of the formation of these structures is distinctive among the peptide pairs, with the SEQ ID NO 10:SEQ ID NO 11 pair reaching equilibrium most rapidly (between 15 min and 1 h) and the SEQ ID NO 9:SEQ ID NO 8 pair taking more than 11 hours before its small-angle scattering pattern becomes evident. The overall gelation kinetics monitored by SAXS follows a clear order of SEQ ID NO 10:SEQ ID NO 11>SEQ ID NO 9:SEQ ID NO 11>SEQ ID NO 10:SEQ ID NO 8>SEQ ID NO 9:SEQ ID NO 8. The order of gelation kinetics can be directly correlated to the total electrostatic and hydrophobic interactions among the oligopeptide pairs, which is highest for the SEQ ID NO 10:SEQ ID NO 11 pair and least for the SEQ ID NO 9:SEQ ID NO 8 pair. Among the two unequal chain length pairs, kinetics of SEQ ID NO 9:SEQ ID NO 11 (13 charged and 12 apolar amino acids) was faster than SEQ ID NO 10:SEQ ID NO 8 (12 charged and 13 apolar amino acids). This difference in gelation kinetics might be attributed to higher electrostatic interactions (longer-range) in the former.

Table 4 summarizes the structural parameters derived from the SAXS data (using Eqn (2)) at two time points: 11 h and 24 h.

TABLE 4

Pair-wise vector length distribution function (P(r)) of four biomaterials.

| Sequences | $R_g$ (Å) 11 h | $R_g$ (Å) 24 h | $d_{max}$ (Å) 11 h | $d_{max}$ (Å) 24 h |
|---|---|---|---|---|
| SEQ ID NO 10:SEQ ID NO 11 | 257 ± 10 | a | 750 | a |
| SEQ ID NO 9:SEQ ID NO 11 | 268 ± 26 | 264 ± 24 | 750 | 750 |
| SEQ ID NO 10:SEQ ID NO 8 | 159 ± 11 | 170 ± 10 | 410 | 450 |
| SEQ ID NO 9:SEQ ID NO 8 | 150 ± 15 | 212 ± 25 | 420 | 650 |

$R_g$ is the radius of gyration and $d_{max}$ is the maximum linear dimension of the hydrogels obtained from P(r) analysis,
a Because there is no measurable difference in the scattering profiles for SEQ ID NO 10:SEQ ID NO 11 between these time points, only the 11 h results are shown.

$R_g$ is the radius of gyration and $d_{max}$ is the maximum linear dimension of the hydrogels obtained from P(r) analysis. (a) Because there is no measurable difference in the scattering profiles for SEQ ID NO 10:SEQ ID NO 11 between these time points, only the 11 h results are shown.

It should be noted that the maximum dimensions ($d_{max}$) of the structures within the hydrogel materials are near, and for the largest structures beyond, the limit of what can be measured accurately given the minimum Q value ($Q_{minimum}=0.0054$ Å$^{-1}$) measured in these experiments. Thus the larger $d_{max}$ values should be viewed as lower limits. The average dimensions of structural features within each hydrogel reveal that the two peptide pairs containing SEQ ID NO 11 gave rise to scattering patterns indicative of larger $R_g$ and $d_{max}$ values, while the two peptides containing SEQ ID NO 8 peptides have significantly smaller $R_g$ and $d_{max}$ values.

Guinier plots for each of the four biomaterials show a "roll-over" in the low-Q region, that is the data begin to fall off with decreasing Q at $Q^2$ values<0.0001 Å$^{-2}$. This effect is characteristic of highly asymmetric particles such as a fiber whose length is much greater than its cross sectional radius (FIG. 5A). The point at which this roll-over begins depends on the aspect ratio (A=L/2R, L is the length of the fiber rod and R is the radius of cross-section of the fiber rod) of the rod-shaped fibers; that is, the higher aspect ratio, the lower the value of Q where the roll-over begins. Higher aspect ratio means longer fibers with respect to their cross sections. Based on the positions of the roll-over points presented in FIG. 19A, SEQ ID NO 10:SEQ ID NO 11, SEQ ID NO 9:SEQ ID NO 11 and SEQ ID NO 10:SEQ ID NO 8 pairs all had higher aspect ratio than the SEQ ID NO 9:SEQ ID NO 8 pair. This result implies that the SEQ ID NO 9:SEQ ID NO 8 pair forms the fibers that have the shortest persistence length among the four oligopeptide pairs. Guinier analysis for elongated or rod-like particles failed to show a single linear region for any of the four peptide pairs, rather there were several linear regions that were indicative of radii of gyration of cross section ($R_c$) values in the range 80-170 Å for the SEQ ID NO 10:SEQ ID NO 11 and SEQ ID NO 9:SEQ ID NO 11 pair, and in the smaller range 40-100 Å for the SEQ ID NO 10:SEQ ID NO 8 and SEQ ID NO 9:SEQ ID NO 8 pair. The 30 nm (300 Å) dimension identified in the TEM figures would give rise to an $R_c$ value of ~106 Å, which is in the range of $R_c$ values seen for peptide pairs with SAXS. Noting the samples used for TEM and SAXS have very different hydration levels, this behavior is analogous to that of cross-β structures whose structure features are not affected by the hydration level of the sample.

Figure 19B:
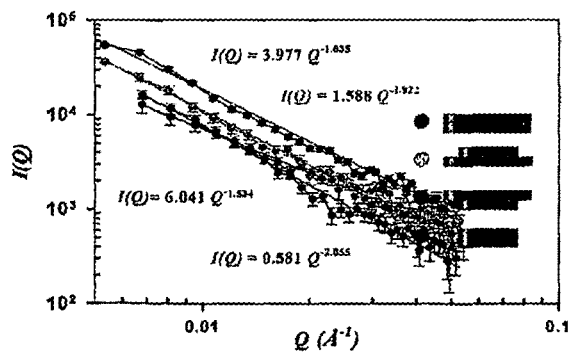

Semi-ordered nanostructures, with a repeating mass unit, can be analyzed using mass fractal power-law decay analysis to explore their morphological characteristics. The Guinier regime probes longer range order corresponding to lower Q region, whereas the power-law regime probes the shorter range order corresponding to higher Q region. Mass-fractal analysis of the scattering data reveals fractal dimensions (i.e., $d_f$ values) between 1.5 and 2.0 (FIG. 19B). On the basis of $d_f$ values' deviation from 2, the canonical value for Gaussian coil, the degrees of swollenness have the order: SEQ ID NO 10:SEQ ID NO 8 (1.5) SEQ ID NO 10:SEQ ID NO 11 (1.8) SEQ ID NO 9:SEQ ID NO 11 (1.9)>SEQ ID NO 9:SEQ ID NO 8 (2.0). Since the TEM image (Supporting Information) shows fibrous structures, disk-shapes can be ruled-out for these biomaterials having fractal dimension near 2, and it appears that the fibers assemble as Gaussian-coils or swollen Gaussian coils, and as a mixture of these forms (FIG. 19B). Note that only the EAW10:KAW10 pair gives a $d_f$ value equal to what is predicted for a true Gaussian coil (i.e., least degree of swollenness) and also forms the strongest hydrogel, suggesting that the presence of the swollen Gaussian coil components play a role in diminishing the strength of the hydrogel. For these kinds of structures, $B_f$ is proportional to the end-to-end distance of the Gaussian coil. The $B_f$ values follow the same order as the $d_f$ values, but in reverse: SEQ ID NO 10:SEQ ID NO 8 (6.0)>SEQ ID NO 10:SEQ ID NO 11 (4.0)>SEQ ID NO 9:SEQ ID NO 11 (1.6)>SEQ ID NO 9:SEQ ID NO 8 (0.6). A larger $B_f$ value signifies, on the average, a longer fiber. These fractal dimensions of these biomaterials are within the range reported in the literature for other heat-set protein gels.

The SAXS data indicate that the SEQ ID NO 9:SEQ ID NO 8 peptide pair is the slowest to form nano-scale structures and is the only peptide pair to show characteristics of a true Gaussian coil in the fractal analysis. Further, the Gunier plot and $B_f$ values indicate its fiber structures have the shortest persistence length. Because the blunt-end SEQ ID NO 9:SEQ ID NO 8 pair forms a stronger hydrogel than sticky-end pairs (from rheological analysis), without wishing to be bound by theory, it is thought that the hydrogels have nano fibers in which the peptide chains are aligned perpendicular to the fiber axis as shown in FIG. 19. It has been previously shown that these oligopeptide fibers bind to the organic dye Congo Red in a fashion similar to that of amyloid fibers. Furthermore, sequences with alternating polar and non-polar sequence patterns are prone to form fibrillar structures similar to β-amyloid. These features suggest that the structures underlying the oligopeptide fibers are similar to that underlying of amyloid fibers, which are cross-β structures. Cross-β structures consist of helical arrays of β-sheet with constitutive β-strands running perpendicular to the helical fiber axis.

In addition to demonstrating that sticky-ends appear to provide no advantage in terms of gel strength, the rheological measurements indicate that of the two blunt-ended pairs, the shorter SEQ ID NO 9:SEQ ID NO 8 pair appears to form a stronger gel than the longer SEQ ID NO 10:SEQ ID NO 11 pair. The reason for this is perhaps due to the structural features of β-strands. Most β-sheet structures found in native proteins and amyloid aggregates have a twisted conformation. For a stable cross-β sheet that can twist into a fiber, the optimum chain length in each β-strand is reported to be in the range of 8 to 12 amino acids. This feature is consistent with the result that the SEQ ID NO 9:SEQ ID NO 8 pair appears to form a stronger gel than the SEQ ID NO 10:SEQ ID NO 11 pair. Note that the longer chain-lengths of proteins that form amyloids are accommodated into the fiber with the polypeptide chain folding back onto itself. In the self-repulsive oligopeptide module, such folding will be prevented because of the electrostatic repulsions and limited chain length. The resulting structure might have dangling ends of peptides in the growing fibers which could affect fibrillogenesis. This example suggests that the optimum oligopeptide chain length for the co-assembly of these biomaterials is around 10.

All of the COMPOSITIONS, METHODS and APPARATUS disclosed and claimed herein can be made and executed without undue experimentation in light of the present disclosure. While the methods and apparatus of this invention have been described in terms of preferred embodiments, it will be apparent to those of skill in the art that variations may be applied to the COMPOSITIONS, METHODS and APPARATUS and in the steps or in the sequence of steps of the methods described herein without departing from the concept, spirit and scope of the invention. More specifically, it will be apparent that certain related components may be substituted for the components described herein while the same or similar results would be achieved. All such similar substitutes and modifications apparent to those skilled in the art are deemed to be within the spirit, scope and concept of the invention as defined by the appended claims.

What is claimed is:

1. A composition comprising a hydrogel capable of self-assembly upon mixing two or more structurally distinct mutually electrostatically complementary peptides, wherein the two or more mutually electrostatically complementary peptides comprise an adjacent alternating charged and neutral residue sequence pattern, wherein the alternating charge on one of the two or more structurally distinct mutually electrostatically complementary peptides is a positively charged residue, wherein the alternating charge on one of the two or more structurally distinct mutually electrostatically complementary peptides is a negatively charged residue, and wherein said hydrogel is capable of regaining mechanical strength after exposure to stress.

2. The composition of claim 1, wherein the two or more mutually electrostatically complementary peptides comprise at least one peptide comprising positive charges and at least one peptide comprising negative charges.

3. The composition of claim 1, wherein the peptides retain bioactivity in situ.

4. The composition of claim 1, wherein said hydrogel is capable of self-assembly and disassembly.

5. The composition of claim 1, wherein the two or more structurally distinct mutually electrostatically complementary peptides comprise a positively charged and a negatively charged peptide.

6. The composition of claim 5, wherein the positively charged peptide is selected from the group consisting of SEQ ID NO: 2, SEQ ID NO: 3, SEQ ID NO: 8, and SEQ ID NO: 11.

7. The composition of claim 6, wherein the negatively charged peptide is selected from the group consisting of SEQ ID NO: 1, SEQ ID NO: 9, and SEQ ID NO: 10.

8. The composition of claim 5, wherein the negatively charged peptide is selected from the group consisting of SEQ ID NO: 1, SEQ ID NO: 9, and SEQ ID NO: 10.

* * * * *

SEQUENCE LISTING

```
<160> NUMBER OF SEQ ID NOS: 11

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: AMIDATION

<400> SEQUENCE: 1

Glu Trp Glu Val Glu Val Glu Val Glu Val
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (15)..(15)
<223> OTHER INFORMATION: AMIDATION

<400> SEQUENCE: 2

Lys Trp Lys Val Lys Val Lys Val Lys Val Lys Val Lys Val Lys
1               5                   10                  15

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: AMIDATION

<400> SEQUENCE: 3

Trp Lys Val Lys Val Lys Val Lys Val Lys
1               5                   10
```

```
<210> SEQ ID NO 4
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: AMIDATION

<400> SEQUENCE: 4

Trp Lys Ser Lys Ser Lys Ser Lys Ser Lys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: AMIDATION

<400> SEQUENCE: 5

Glu Trp Glu Ser Glu Ser Glu Ser Glu Ser
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: AMIDATION

<400> SEQUENCE: 6

Trp Lys Pro Lys Pro Lys Pro Lys Pro Lys
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: AMIDATION

<400> SEQUENCE: 7
```

Glu Trp Glu Pro Glu Pro Glu Pro Glu Pro
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: AMIDATION

<400> SEQUENCE: 8

Trp Lys Ala Lys Ala Lys Ala Lys Ala Lys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: AMIDATION

<400> SEQUENCE: 9

Glu Trp Glu Ala Glu Ala Glu Ala Glu Ala
1               5                   10

<210> SEQ ID NO 10
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (15)..(15)
<223> OTHER INFORMATION: AMIDATION

<400> SEQUENCE: 10

Trp Glu Ala Glu Ala Glu Ala Glu Ala Glu Ala Glu Ala Glu Ala
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:

```
<221> NAME/KEY: MOD_RES
<222> LOCATION: (15)..(15)
<223> OTHER INFORMATION: AMIDATION

<400> SEQUENCE: 11

Lys Trp Lys Ala Lys Ala Lys Ala Lys Ala Lys Ala Lys Ala Lys
1               5                   10                  15
```